United States Patent [19]

Garwood et al.

[11] 4,227,992
[45] Oct. 14, 1980

[54] PROCESS FOR SEPARATING ETHYLENE FROM LIGHT OLEFIN MIXTURES WHILE PRODUCING BOTH GASOLINE AND FUEL OIL

[75] Inventors: William E. Garwood, Haddonfield; Wooyoung Lee, Cherry Hill, both of N.J.

[73] Assignee: Mobil Oil Corporation, New York, N.Y.

[21] Appl. No.: 41,843

[22] Filed: May 24, 1979

[51] Int. Cl.$^3$ ............................................. C10G 35/06
[52] U.S. Cl. ....................................... 208/46; 208/71; 208/135; 585/650; 585/800
[58] Field of Search ........................... 208/46, 71, 135; 585/650, 800

[56] References Cited

U.S. PATENT DOCUMENTS

| | | | |
|---|---|---|---|
| 2,408,010 | 9/1946 | Wadley et al. | 585/800 |
| 3,760,024 | 9/1973 | Cattanach | 585/415 |
| 3,827,968 | 8/1974 | Givens et al. | 585/322 |
| 3,960,978 | 6/1976 | Givens et al. | 585/533 |

*Primary Examiner*—Herbert Levine
*Attorney, Agent, or Firm*—Charles A. Huggett; Raymond W. Barclay

[57] ABSTRACT

A process is disclosed for separating ethylene in admixture with light olefins by contacting said olefinic mixture under very critical reaction conditions over a special catalyst, such as a zeolite of the ZSM-5 type so as to selectively react the $C_3$ and higher olefins and convert the same to both gasoline and fuel oil.

8 Claims, 2 Drawing Figures

Conversion of $C_2^=/C_3^=$ Mixture over HZSM-5B 400 psig
0.4–0.6 WHSV $C_2^=$
0.4 WHSV $C_3^=$
6–8 Days on stream ○ $C_2^=$ Conversion, wt.%
● $C_3^=$ Conversion, wt.%

AVERAGE CATALYST TEMPERATURE, °F

Product composition from $C_2^=/C_3^=$ Conversion Versus Temperature

PROCESS FOR SEPARATING ETHYLENE FROM LIGHT OLEFIN MIXTURES WHILE PRODUCING BOTH GASOLINE AND FUEL OIL

BACKGROUND OF THE INVENTION

This invention relates to the separation of ethylene from a mixture of the same with light olefins by contacting said mixture with a special group of acidic crystalline aluminosilicate zeolites, such as those of the ZSM-5 type in order to selectively convert $C_3$ and higher olefins into products comprising both gasoline and fuel oil while substantially not affecting the conversion of ethylene. The ethylene can then be recovered by simply flashing it off from the higher boiling product.

There are many processes known in the patent and technical literature, as well as in commercial operation which give a mixture of light hydrocarbons comprising ethylene and higher olefins. Thus, by way of illustration, catalytic cracking processes involving the catalytic cracking of gas oil, as well as thermal cracking processes of light paraffins, naphtha, and gas oils all result in mixtures of ethylene with higher olefins. A more recent process resulting in the production of olefinic mixtures containing ethylene involves the conversion of methanol over a ZSM-5 type zeolite. This process is described in *Journal of Catalysis,* Vol. 56, pages 169-173 (1979). Methanol conversion over ZSM-5 type zeolites is important in areas of the world that are short of petroleum crudes since methanol is produced from synthesis gas comprising mixtures of hydrogen and carbon oxides which, in turn, is produced by the gasification of natural gas or coal, etc.

DESCRIPTION OF THE PRIOR ART

The conventional way of separating ethylene from a mixture of the same with higher light olefins is by distillation columns which is a relatively expensive technique. It is also to be specifically noted that the broad concept of contacting an olefinic charge stock containing ethylene with the special class of zeolites with which this invention is concerned is known in the art and is the subject of various U.S. patents. Thus, for example, U.S. Pat. No. 3,960,978 teaches conversion of olefins to olefinic gasolines. U.S. Pat. No. 4,021,502 discloses conversion of olefins over ZSM-12. U.S. Pat No. 3,760,024 discloses contacting olefins with ZSM-5 type zeolites. U.S. Pat. No. 3,775,501 discloses preparation of aromatics by contacting olefins over ZSM-5 type catalysts. U.S. Pat. No. 3,827,968 discloses a two-step aromatization process wherein in the first step an olefin is contacted over a ZSM-5 type zeolite. However, none of the prior art is directed towards the concept of selectively reacting $C_3$ and higher olefins from a mixture of the same with ethylene to yield reaction products comprising both fuel oil and gasoline.

DESCRIPTION OF THE PREFERRED EMBODIMENTS

Figure 1:
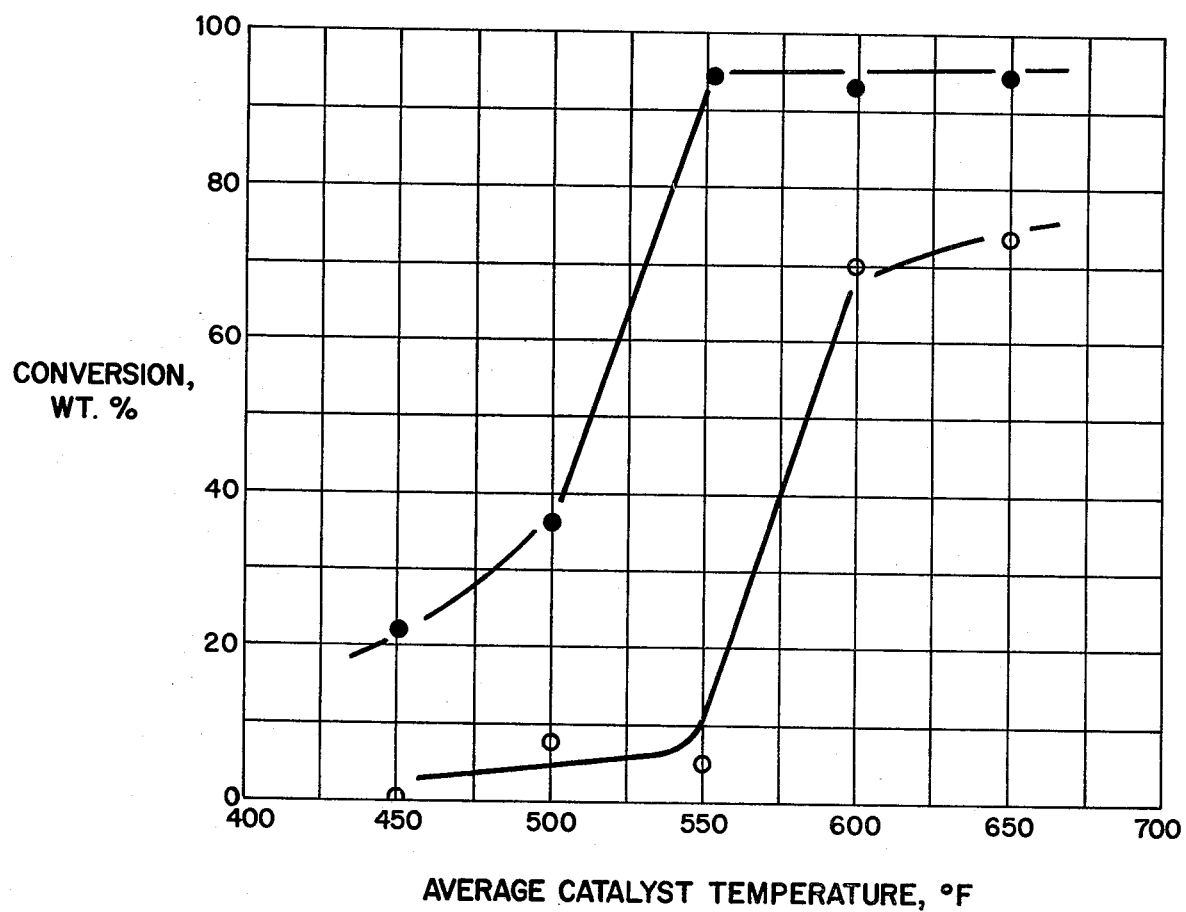
FIG. 1 represents a plot of the conversion of ethylene and propylene mixtures.

The novel process of this invention is directed towards contacting a mixture of ethylene and propylene which can also contain other light olefins, up to and inclusive of $C_5$ and which can also contain other hydrocarbons, such as paraffins with a special class of zeolites under very specific reaction conditions so as to selectively react olefins other than ethylene and produce both gasoline and fuel oil.

The acidic crystalline aluminosilicate utilized is characterized by a pore dimension greater than about 5 Angstroms, i.e. it is capable of sorbing paraffins having a single methyl branch as well as normal paraffins, and it has a silica-to-alumina ratio of at least 2.5. Zeolite A, for example, with a silica-to-alumina ratio of 2.0 is not useful in this invention, and it has no pore dimension greater than about 5 Angstroms.

The crystalline aluminosilicates herein referred to, also known as zeolites, constitute an unusual class of natural and synthetic minerals. They are characterized by having a rigid crystalline framework structure composed of an assembly of silicon and aluminum atoms, each surrounded by a tetrahedron of shared oxygen atoms, and a precisely defined pore structure. Exchangeable cations are present in the pores.

Zeolites useful for the crystalline aluminosilicate component of this invention include the acidic forms of: zeolite X, described in U.S. Pat. No. 2,882,244; zeolite Y, described in U.S. Pat. No. 3,130,007; mordenite; zeolite L, described in U.S. Pat. No. 3,216,789; zeolite T, described in U.S. Pat. No. 2,950,952; and zeolite beta, described in U.S. Pat. No. 3,308,069. The acidic crystalline aluminosilicate component should be in the hydrogen form, or it may be stabilized by ion exchange with rare earth or other metal cations.

The preferred zeolites useful in this invention are selected from a recently discovered novel class of zeolites with unusual properties. These zeolites by themselves can induce profound catalytic transformations of aliphatic hydrocarbons to aromatic hydrocarbons. Although they have unusually low alumina contents, i.e. high silica-to-alumina ratios, they are very active even when the silica-to-alumina ratio exceeds 30. The activity is surprising since the alumina in the zeolite framework is believed responsible for catalytic activity. These catalysts retain their crystallinity for long periods in spite of the presence of steam at high temperature which induces irreversible collapse of the framework of other zeolites, e.g. of the X and A type. Furthermore, carbonaceous deposits, when formed, may be removed by burning at higher than usual temperatures to restore activity. Equally important, when used as the acidic crystalline aluminosilicate component in the process of this invention, catalytic activity is sustained for unusually long periods of time.

An important characteristic of the crystal structure of this preferred class of zeolites is that is provides constrained access to, and egress from, the intracrystalline free space by virtue of having a pore dimension greater than about 5 Angstroms and pore windows of about a size such as would be provided by 10-membered rings of oxygen atoms. It is to be understood, of course, that these rings are those formed by the regular disposition of the tetrahedra making up the anionic framework of the crystalline aluminosilicate, the oxygen atoms themselves being bonded to the silicon or aluminum atoms at the centers of the tetrahedra. Briefly, the preferred acidic crystalline aluminosilicates useful in this invention possess, in combination: a silica-to-alumina ratio of at least about 12; and a structure providing constrained access to the intracrystalline free space.

The silica-to-alumina ratio referred to may be determined by conventional analysis. This ratio is meant to represent, as closely as possible, the ratio in the rigid anionic framework of the zeolite crystal and to exclude alumina in the binder or in cationic form within the channels. Although acidic crystalline aluminosilicates with a silica-to-alumina ratio of at least 12 are useful, it is preferred to use those having higher ratios of at least about 30. Such solids, after activation, acquire an intracrystalline sorption capacity for normal hexane which is greater than that for water, i.e. they exhibit "hydrophobic" properties. It is believed that this hydrophobic character is advantageous in the present invention.

The preferred crystalline aluminosilicates useful in this invention freely sorb normal hexane and have a pore dimension greater than about 5 Angstroms. In addition, the structure must provide constrained across to larger molecules. It is sometimes possible to judge from a known crystal structure whether such constrained access exists. For example, if the only pore windows in a crystal are formed by eight-membered rings or oxygen atoms, then access to molecules of larger cross-section than normal hexane is excluded and the zeolite is not of the desired type. Windows of ten-membered rings are preferred, although excessive puckering or pore blockage may render these catalysts ineffective. Twelve-membered rings do not generally appear to offer sufficient constraint to produce the advantageous selectivity, although structures can be conceived, due to pore blockage or other cause, that may be operative.

Rather than attempt to judge from crystal structure whether or not a zeolite possesses the necessary constrained access, a simple determination of the "constraint index" may be made by passing continuously a mixture of equal weight of normal hexane and 3-methylpentane over a small sample, approximately 1 gram or less, of catalyst at atmospheric pressure according to the following procedure. A sample of the catalyst, in the form of pellets or extrudate, is crushed to a particle size about that of coarse sand and mounted in a glass tube. Prior to testing, the catalyst is treated with a stream of air at 1000° F. for at least 15 minutes. The catalyst is then flushed with helium and the temperature adjusted between 550° F. and 950° F. to give an overall conversion between 10 and 60 percent. The mixture of hydrocarbons is passed at 1 liquid hourly space velocity (i.e. 1 volume of hydrocarbon per volume of catalyst per hour) over the catalyst with a helium dilution to give a helium to total hydrocarbon mole ratio of 4:1. After 20 minutes on stream, a sample of the effluent is taken and analyzed, most conveniently by gas chromatography, to determine the fraction remaining unchanged for each of the two hydrocarbons.

The "constraint index" is calculated as follows:

$$\text{Constraint Index} = \frac{\log_{10}(\text{fraction of n-hexane remaining})}{\log_{10}(\text{fraction of 3-methylpentane remaining})}$$

The constraint index approximates the ratio of the cracking rate constants for the two hydrocarbons. Catalysts suitable for the present invention are those having a constraint index from 1.0 to 12.0, preferably 2.0 to 7.0.

The preferred class of zeolites defined herein is exemplified by ZSM-5, ZSM-11, ZSM-12, ZSM-21, TEA mordenite and other similar materials. Recently issued U.S. Pat. No. 3,702,886 describing and claiming ZSM-5 is incorporated herein by reference.

ZSM-11 is more particularly described in U.S. Pat. No. 3,709,979, the entire contents of which are incorporated herein by reference.

ZSM-12 is more particularly described in U.S. Pat. No. 3,832,449, the entire contents of which are incorporated herein by reference.

ZSM-21 is more particularly described in U.S. Application Ser. No. 358,192, filed May 7, 1973 the entire contents of which are incorporated herein by reference, which application has been abandoned in favor of U.S. Application Ser. Nos. 528,060 and 528,061, filed Nov. 29, 1974 directed to ZSM-38 and 35 respectively, the apparent component zeolites of ZSM-21, the entire contents of which are incorporated herein by reference. Ser. No. 528,061 has matured into U.S. Pat. No. 4,016,245. Ser. No. 528,060 has been abandoned in favor of Ser. No. 560,412 which has matured into U.S. Pat. No. 4,046,859.

The specific preferred zeolites described, when prepared in the presence of organic cations, are catalytically inactive, possibly because the intracrystalline free space is occupied by organic cations from the forming solution. They may be activated by heating in an inert atmosphere at 1000° F. for 1 hour, for example, followed by base exchange with ammonium salts followed by calcination at 1000° F. in air. The presence of organic cations in the forming solution may not be absolutely essential to the formation of this special type zeolite; however, the presence of these cations does appear to favor its formation. Regardless of preparation technique, it is desirable to activate this type of zeolite by base exchange with ammonium salts followed by calcination in air at about 1000° F. for from about 15 minutes to about 24 hours.

Natural zeolites may sometimes be converted to this preferred type zeolite by various activation procedures and other treatments such as base exchange, steaming, alumina extraction and calcination, in combinations. Natural minerals which may be so treated include ferrierite, brewsterite, stillbite, dachiardiate, epistilbite, heulandite, and clinoptilolite. The preferred crystalline aluminosilicates are ZSM-5, ZSM-11, ZSM-12, ZSM-21 and TEA mordenite, with ZSM-5 particularly preferred.

The preferred acidic crystalline aluminosilicates components are those having a crystal density, in the dry hydrogen form, of not substantially below about 1.6 grams per cubic centimeter. It has been found that zeolites which satisfy all three of these criteria are most desired. Therefore, the preferred zeolites are those having a constraint index as defined above of about 1 to 12, a silica-to-alumina ratio of at least about 12 and a dried crystal density of not less than about 1.6 grams per cubic centimeter. The dry density for known structures may be calculated from the number of silicon plus aluminum atoms per 1000 cubic Angstroms, as given, e.g. on page 11 of the article of Zeolite Structure by W. M. Meier. This paper, the entire contents of which are incorporated herein by reference, is included in "Proceedings of the Conference on Molecular Sieves," London, April 1967, published by the Society of Chemical Industry, London, 1968. When the crystal structure is unknown, the crystal framework density may be determined by classical pyknometer techniques. For example, it may be determined by immersing the dry hydrogen form of the zeolite in an organic solvent which is not sorbed by the crystal. It is possible that the unusual sustained activity and stability of this class of zeolites is associated with its high crystal anionic framework density of not less than about 1.6 grams per cubic centimeter. This high density, of course, must be associated with a relatively small amount of free space within the crystal, which might be expected to result in more stable structures. This free space, however, is important as the locus of catalytic activity.

The crystalline aluminosilicate of this invention in all cases should be acidic as evidenced by some degree of catalytic activity for cracking of normal hexane. The degree of acidity as evidenced in a hexane-cracking test which gives an alpha value of at least 10 and, more preferably, at least 100 is required. The alpha value is to be determined in accordance with the method set forth by P. B. Weisz and J. N. Miale in "Journal of Catalysis", Vol, 4, No. 4, August 1969, pp. 527–529, which description is herein incorporated by reference. The alpha value is determined before this component is formed into an intimate mixture with the carbon monoxide reducing component.

As has heretofore been stated, the broad concept of contacting olefins, including mixtures of ethylene with higher olefins over the identical catalyst with which this invention is concerned is not per se novel. The entire key to the inventive concept of this invention resides in choosing a certain limited critical range of operating conditions such that the following three objectives will be accomplished:

(1) $C_3$ and higher olefins will be substantially converted, i.e. greater than about 80 and preferably greater than about 90 weight percent;

(2) substantially no ethylene will be converted, i.e. less than 20 weight percent and more preferably less than 10 weight percent;

(3) the products obtained will comprise both fuel oil and gasoline.

The general operating parameters for carrying out the novel process of this invention can be defined by stating that the process is carried out at pressures from about 100 to 1000 psig, at temperatures ranging from 300° to 600° F., and at space velocities of 0.1 to 10 WHSV, based on the $C_3$ and higher olefins. It is to be immediately understood that the above recitation of ranges of pressure, space velocity, and temperature is not intended to mean that all operations within the above set forth limits will result in producing the desired results of the instant invention. On the contrary, what is meant by the above limits concerning temperature, pressure and space velocity is best expressed in a negative way. Operations outside the ranges specifically set forth will not result in the improved process of this invention. It is well known in the art that there is a correlation between temperature, pressure and space velocity with respect to the severity of a given chemical reaction. Quite simply put, the instant invention is concerned with conversion of ethylene in admixture with propylene and higher olefins at a severity such that substantially only the olefins other than ethylene are converted and that said conversion results in the production of both fuel oil and gasoline. Thus, by way of specific illustration, reference is made to FIG. 1 which represents a plot of the conversion of ethylene and propylene over acid HZSM-5 at a temperature of 400 psig, and a space velocity of 0.4 WHSV with respect to the propylene at various temperatures. As can be seen from said FIG. 1, at the pressure and space velocity specified, a temperature of 550° F. resulted in the conversion of less than about 10 weight percent ethylene and a conversion of greater than 90 weight percent propylene. This is precisely the severity which is desirable in the instant operation. It is also known in the art that if the pressure remains constant and the space velocity is increased, then a higher temperature is necessary to achieve the desired severity. Thus, again with reference to FIG. 1, if the space velocity of the $C_3$ and higher olefins were to be increased and the pressure remain constant, it would take a higher temperature than 550° F. to achieve that point at which more than about 90 weight percent of propylene were converted and less than about 10 weight percent of ethylene were converted. Conversely, if the space velocity were to remain constant and the pressure increased, there would be a corresponding decrease of the temperature required to achieve the relative conversion previously set forth.

Thus, it is not possible to define the operating parameters of this invention merely by reciting a range of temperatures, pressures and space velocities. It is also necessary to state that within the range of pressure, temperature and space velocity a severity must be achieved which is sufficient to ensure conversion of at least 80 weight percent of the $C_3+$ olefins less than about 20 weight percent of the ethylene.

It appears quite obvious that the precise space velocity and pressure for any given temperature within the broad range previously referred can be easily obtained by routine experimentation following the guidelines above set forth.

It should also be obvious that since the instant invention is directed towards the process for the selective separation of ethylene from a mixture of the same with other olefins that there should be significant amounts of ethylene present in the olefin mixture in order to make the instant process attractive. In this connection, it is preferred that ethylene comprise at least 10 weight percent based on the total weight of olefins present in the hydrocarbon mixture. More particularly, it is preferred that the ethylene range from 20 to 50 weight percent, based on the total weight of olefins.

It is to be understand that although this invention has been stated to be applicable to the selective separation of ethylene from mixtures thereof with $C_3$–$C_5$ olefins, as a practical matter the most significant olefin other than ethylene which is usually present in the olefin mixture is propylene. This is because butylene and pentenes are usually removed from olefinic mixtures in hydrocarbon operations and channeled to other uses. Thus, the olefinic mixtures with which this invention is particularly concerned are those comprising ethylene and propylene having minor amounts of $C_4$ and $C_5$ present therein. It is also to be noted that the presence of $C_4$ and $C_5$ olefins has absolutely no effect with regard to the selective removal of ethylene due to the fact that these olefins are converted at conditions which are even less severe than those necessary for propylene. Thus, by the recitation of the positive requirements that at least 80% of the propylene be converted this assures that at least 80% of the $C_4$ and $C_5$ olefins if present would also be converted.

EXAMPLE 1

Catalyst Preparation

The HZSM-5 zeolite catalyst used in the examples was prepared by mixing a dried as synthesized ZSM-5 zeolite having a silica/alumina ratio of about 70 with alumina and water, extruding into 1/16" diameter pellets. The extruded material contained 35 or 65 parts ZSM-5 per 65 or 35 parts alumina.

The dried extrudate was calcined for three hours at 538° C. in flowing nitrogen. After cooling, the extrudate was contacted with an ammonium nitrate exchange solution (about 0.3 lb NH₄NO₃/lb extrudate) for one hour at ambient temperature. This exchange was then repeated until the sodium level was less than 0.5 weight percent. The extrudate was then washed, dried and calcined in flowing air at 538° C. for three hours. The extrudate was then sized to 30–60 mesh.

EXAMPLE 2–6

Ethylene alone was contacted with the extruded catalyst of Example 1 containing 35% ZSM-5 at atmospheric pressure at various temperatures. The results obtained, as well as specific operating conditions are shown in the following table:

TABLE

| Example | 2 | 3 | 4 | 5 | 6 |
|---|---|---|---|---|---|
| WHSV, $C_2=$ | 0.4 | 0.5 | 0.4 | 0.3 | 0.4 |
| Temp., °F., | | | | | |
| Average | 519 | 550 | 576 | 604 | 620 |
| Maximum | 524 | 553 | 580 | 608 | 634 |
| Run Time, Hours | 22 | 22 | 68 | 24 | 70.5 |
| Accumulative Time, Days | 0.9 | 1.9 | 4.7 | 5.7 | 8.6 |
| $C_2=$ Conversion, Wt % | 47 | 70 | 53 | 57 | 62 |
| Liquid Product, Gravity, °API | — | 57.3 | 59.5 | 57.8 | 60.4 |
| Specific | — | 0.7495 | 0.7397 | 0.7475 | 0.7374 |
| Yields, Wt. % | | | | | |
| $C_1$ | <0.1 | <0.1 | <0.1 | <0.1 | <0.1 |
| $C_2$ | 0.2 | 0.2 | 0.3 | 0.6 | 0.3 |
| $C_2=$ | 52.6 | 29.6 | 46.5 | 42.5 | 38.2 |
| $C_3$ | 0.8 | — | 1.5 | 1.8 | 1.3 |
| $C_3=$ | 2.5 | 0.2 | 5.4 | 6.4 | 5.4 |
| $i-C_4$ | 2.8 | 7.2 | 3.2 | 4.4 | 3.9 |
| $n-C_4$ | 0.2 | 1.1 | 0.3 | 0.3 | 0.4 |
| $C_4=$ | 7.6 | 17.5 | 4.3 | 5.5 | 6.6 |
| $i-C_5$ | 2.3 | 4.0 | 1.9 | 2.1 | 2.6 |
| $n-C_5$ | 0.4 | 0.6 | 0.3 | 0.3 | 0.5 |
| $C_5=$ | 9.3 | 12.2 | 5.7 | 4.9 | 7.9 |
| $C_6+$ | 21.3 | 27.4 | 30.6 | 31.2 | 32.9 |
| | 100.0 | 100.0 | 100.0 | 100.0 | 100.0 |
| Liquid Product Boiling Range, °F. | | | | | |
| 10% | — | 103 | 90 | 99 | 100 |
| 30 | — | 160 | 153 | 162 | 165 |
| 50 | — | 236 | 212 | 234 | 238 |
| 70 | — | 296 | 287 | 291 | 292 |
| 90 | — | 396 | 375 | 375 | 375 |
| 95 | — | 445 | 426 | 423 | 421 |
| 98 | — | 493 | 478 | 478 | 467 |
| % Boiling Above 330° F. | — | 21 | 18 | 19 | 19 |
| % Boiling Above 380° F. | — | 12 | 9 | 9 | 9 |
| $C_6+$ Aromatics, Wt. % | <1 | 1 | 1 | 16 | 16 |
| Liquid Product O.N., R + O | — | — | 93.7 | — | 94.8 |

EXAMPLES 7–12

Ethylene alone was contacted with the extruded catalyst of Example 1 containing 35% ZSM-5 at 400 psig at various temperatures. The results obtained, as well as specific operating conditions are shown in the following table.

TABLE

| Example | 7 | 8 | 9 | 10 | 11 | 12 |
|---|---|---|---|---|---|---|
| WHSV, $C_2=$ | 0.4 | 0.4 | 0.4 | 0.4 | 0.4 | 0.4 |
| Temp., °F., | | | | | | |
| Average | 572 | 573 | 576 | 581 | 611 | 631 |
| Maximum | 578 | 588 | 599 | 597 | 626 | 650 |
| Run Time, Hours | 23 | 43 | 100 | 22.5 | 23 | 22.5 |
| Accumulative Time, Days | 1.0 | 2.8 | 6.9 | 7.8 | 8.8 | 9.7 |
| $C_2=$ Conversion, Wt % | | | 66 | 47 | 62 | 79 |
| Liquid Product Gravity, °API | 44.0 | 47.6 | 51.4 | 56.3 | 54.7 | 53.0 |
| Specific | 0.8063 | 0.7901 | 0.7736 | 0.7535 | 0.7599 | 0.7669 |
| Yields, Wt. % | | | | | | |
| $C_1$ | 0.3 | 0.2 | <0.1 | <0.1 | 0.1 | 0.1 |
| $C_2$ | 12.8 | 10.1 | 1.6 | 1.3 | 1.7 | 3.4 |
| $C_2=$ | 2.8 | 7.9 | 34.5 | 52.9 | 37.9 | 21.4 |
| $C_3$ | 5.3 | 1.6 | 0.3 | 0.2 | 0.3 | 1.0 |
| $C_3=$ | 1.5 | 1.4 | 0.6 | 0.6 | 0.5 | 1.3 |
| $i-C_4$ | 6.8 | 4.6 | 1.8 | 1.3 | 1.5 | 2.5 |
| $n-C_4$ | 1.0 | 0.7 | 0.3 | 0.1 | 0.1 | 0.4 |
| $C_4=$ | 2.1 | 1.6 | 1.3 | 1.7 | 1.5 | 2.0 |
| $i-C_5$ | 6.5 | 6.2 | 3.3 | 1.4 | 1.8 | 3.2 |
| $n-C_5$ | 2.0 | 1.3 | 0.5 | 0.2 | 0.2 | 0.7 |
| $C_5=$ | 0.5 | 1.4 | 3.3 | 3.8 | 4.4 | 3.1 |

TABLE-continued

| Example | 7 | 8 | 9 | 10 | 11 | 12 |
|---|---|---|---|---|---|---|
| $C_6+$ | 58.3 | 62.9 | 52.5 | 36.5 | 50.0 | 60.9 |
|  | 100.0 | 100.0 | 100.0 | 100.0 | 100.0 | 100. |
| Liquid Product Boiling Range, °F. | | | | | | |
| 10% | 136 | 134 | 111 | 127 | 131 | 123 |
| 30 | 250 | 240 | 202 | 206 | 181 | 215 |
| 50 | 361 | 331 | 289 | 283 | 291 | 291 |
| 70 | 481 | 441 | 380 | 363 | 367 | 361 |
| 90 | 633 | 587 | 501 | 473 | 466 | 459 |
| 95 | 697 | 647 | 545 | 516 | 507 | 505 |
| 98 | 739 | 689 | 582 | 560 | 545 | 547 |
| % Boiling Above 330° F. | 56 | 50 | 41 | 38 | 40 | 39 |
| % Boiling Above 380° F. | 46 | 40 | 30 | 26 | 27 | 25 |

From the above Examples, it can be seen that at about 575° F. and 5-7 days on stream, greater than 50% of the ethylene was converted both at atmospheric pressure (Example 4) and at 400 psig (Example 9). However, at atmospheric pressure only 18% of liquid product boiled above 330° F. compared to 41% at 400 psig.

It is to be noted that at all the above conditions in which complete data is presented, i.e. Examples 2-6 and 8-12, conversion of ethylene was too high.

EXAMPLES 13-18

Propylene alone was passed over the extruded catalyst of Example 1 containing 65% ZSM-5 at various pressures, temperatures and with and without diluents. The results obtained, as well as specific operating conditions are shown in the following table.

TABLE

| Example | 13 | 14 | 15 | 16 | 17 | 18 |
|---|---|---|---|---|---|---|
| Total Pressure, psig | ← | ← | 700 | → | → | 15 |
| Diluent Gas | ← | $H_2$ | → | $N_2$ | $H_2$ | None |
| Mole Ratio, Diluent Gas/$C_3=$ | 1.1 | 1.1 | 1.1 | 1.2 | 1.6 | — |
| WHSV, $C_3=$ | 0.7 | 0.7 | 0.7 | 0.7 | 0.7 | 0.7 |
| Partial Pressure $C_3=$, psig | 330 | 330 | 330 | 320 | 270 | 15 |
| Temp., °F., Average | 402 | 450 | 501 | 504 | 502 | 526 |
| Maximum | 403 | 451 | 505 | 507 | 504 | 530 |
| Run Time, Hours | 20.5 | 22 | 22 | 20.5 | 21 | 22 |
| Accumulative Time, Days | 0.9 | 1.9 | 2.5 | 8.4[1] | 9.3 | 10.2 |
| $C_3=$ Conversion, Wt. % | 98 | 99 | 99 | 99 | 99 | 99 |
| Liquid Product Gravity, °API | 48.1 | 47.3 | 47.4 | 49.1 | 51.4 | 62.7 |
| Specific | 0.7879 | 0.7914 | 0.7909 | 0.7835 | 0.7736 | 0.7286 |
| Yields, Wt. % | | | | | | |
| $C_1$ | <0.1 | <0.1 | <0.1 | <0.1 | <0.1 | <0.1 |
| $C_2$ | <0.1 | <0.1 | <0.1 | <0.1 | <0.1 | <0.1 |
| $C_2=$ | <0.1 | <0.1 | <0.1 | <0.1 | <0.1 | <0.1 |
| $C_3$ | 2.3 | 2.4 | 4.7 | 1.1 | 2.5 | 0.2 |
| $C_3=$ | 1.8 | <0.1 | 0.4 | 0.1 | 1.2 | 0.5 |
| i-$C_4$ | 0.2 | <0.1 | 1.1 | 0.6 | 0.9 | 0.2 |
| n-$C_4$ | <0.1 | 0.5 | 1.6 | 0.1 | 0.3 | 0.1 |
| $C_4=$ | <0.1 | <0.1 | 0.2 | 0.4 | 1.2 | 4.3 |
| i-$C_5$ | 0.5 | 2.5 | 3.5 | 1.2 | 1.3 | 0.3 |
| n-$C_5$ | <0.1 | 0.9 | 2.3 | 0.3 | 0.2 | 0.1 |
| $C_5=$ | <0.1 | 0.9 | 1.1 | 2.4 | 4.1 | 11.0 |
| $C_6+$ | 95.2 | 91.7 | 85.1 | 93.5 | 88.2 | 83.3 |
|  | 100.0 | 100.0 | 100.0 | 100.0 | 100.0 | 100.0 |
| Liquid Product Boiling Range, °F. | | | | | | |
| 10% | 236 | 191 | 142 | 242 | 189 | 107 |
| 30 | 325 | 308 | 290 | 352 | 297 | 164 |
| 50 | 388 | 392 | 427 | 446 | 395 | 233 |
| 70 | 462 | 474 | 568 | 540 | 493 | 295 |
| 90 | 534 | 553 | 741 | 685 | 654 | 379 |
| 95 | 559 | 571 | 801 | 750 | 729 | 421 |
| 98 | 571 | 583 | 853 | 806 | 791 | 465 |
| % Boiling Above 330° F. | 70 | 66 | 65 | 73 | 64 | 23 |
| % Boiling Above 380° F. | 54 | 55 | 58 | 64 | 54 | 9 |

[1] Unstable operation between 3 and 7 days, temperature 400°-600° F.

From the above table, it can be seen that essentially complete conversion of propylene was obtained under all conditions tested. However, more 330° F+ fuel oil was made when the reaction was run under pressure than was made at atmospheric pressure. Additionally, less $C_4$'s are produced when the reaction is run under pressure.

EXAMPLES 19-23

A mixture of ethylene and propylene (approximately equal parts by weight) was passed over the extruded catalyst of Example 1 containing 65% ZSM-5 at 400 psig and at various temperatures. The actual operating conditions, as well as results are shown in the following table:

TABLE

| Example | 19 | 20 | 21 | 22 | 23 |
|---|---|---|---|---|---|
| $C_2=$, WHSV | 0.6 | 0.6 | 0.5 | 0.4 | 0.5 |
| $C_3=$, WHSV | 0.4 | 0.4 | 0.4 | 0.4 | 0.4 |
| Temp., °F. | | | | | |
| Average | 452 | 500 | 553 | 599 | 650 |
| Maximum | 457 | 506 | 558 | 605 | 658 |
| Run Time, Hours | 19½ | 5 | 16½ | 5 | 16½ |
| Accumulative Time, Days | 6.5 | 6.7 | 7.4 | 7.6 | 8.3 |
| Liquid Product Gravity, °API | — | — | 56.7 | 58.4 | 56.7 |
| $C_2=$ Conversion, wt. % | 21 | 7 | 5 | 70 | 74 |
| $C_3=$ Conversion, wt. % | 22 | 36 | 95 | 93 | 95 |
| Yields, Wt. % | | | | | |
| $C_1$ | <0.1 | <0.1 | <0.1 | <0.1 | <0.1 |
| $C_2$ | <0.1 | <0.1 | <0.1 | 0.1 | 0.7 |
| $C_2=$ | 60.0 | 55.0 | 52.0 | 14.9 | 13.9 |
| $C_3$ | 0.6 | 0.9 | 0.6 | 0.5 | 1.0 |
| $C_3=$ | 31.3 | 26.2 | 2.3 | 3.5 | 2.2 |
| $i-C_4$ | 0.6 | 1.1 | 0.3 | 0.8 | 1.4 |
| $n-C_4$ | 0.3 | 0.2 | 0.1 | 0.3 | 0.5 |
| $C_4=$ | 0.4 | 0.7 | 1.2 | 1.3 | 1.4 |
| $i-C_5$ | 0.2 | 0.2 | 0.2 | 0.7 | 2.3 |
| $n-C_5$ | <0.1 | <0.1 | <0.1 | 0.2 | 0.8 |
| $C_5=$ | 0.8 | 2.0 | 3.5 | 4.7 | 4.6 |
| $C_6+$ | 5.8 | 13.7 | 39.8 | 73.0 | 71.2 |
| | 100.0 | 100.0 | 100.0 | 100.0 | 100.0 |
| Liquid Product Boiling Range, °F. | | | | | |
| 10% | 223 | 153 | 140 | 149 | 116 |
| 30 | 317 | 248 | 218 | 218 | 208 |
| 50 | 670 | 340 | 276 | 281 | 277 |
| 70 | 730 | 678 | 333 | 330 | 334 |
| 90 | 778 | 750 | 407 | 397 | 402 |
| 95 | 793 | 770 | 437 | 421 | 424 |
| 98 | 805 | 785 | 457 | 437 | 440 |
| % Boiling Above 330° F. | 68 | 51 | 31 | 30 | 32 |
| % Boiling Above 380° F. | 63 | 44 | 16 | 14 | 15 |

Figure 2:
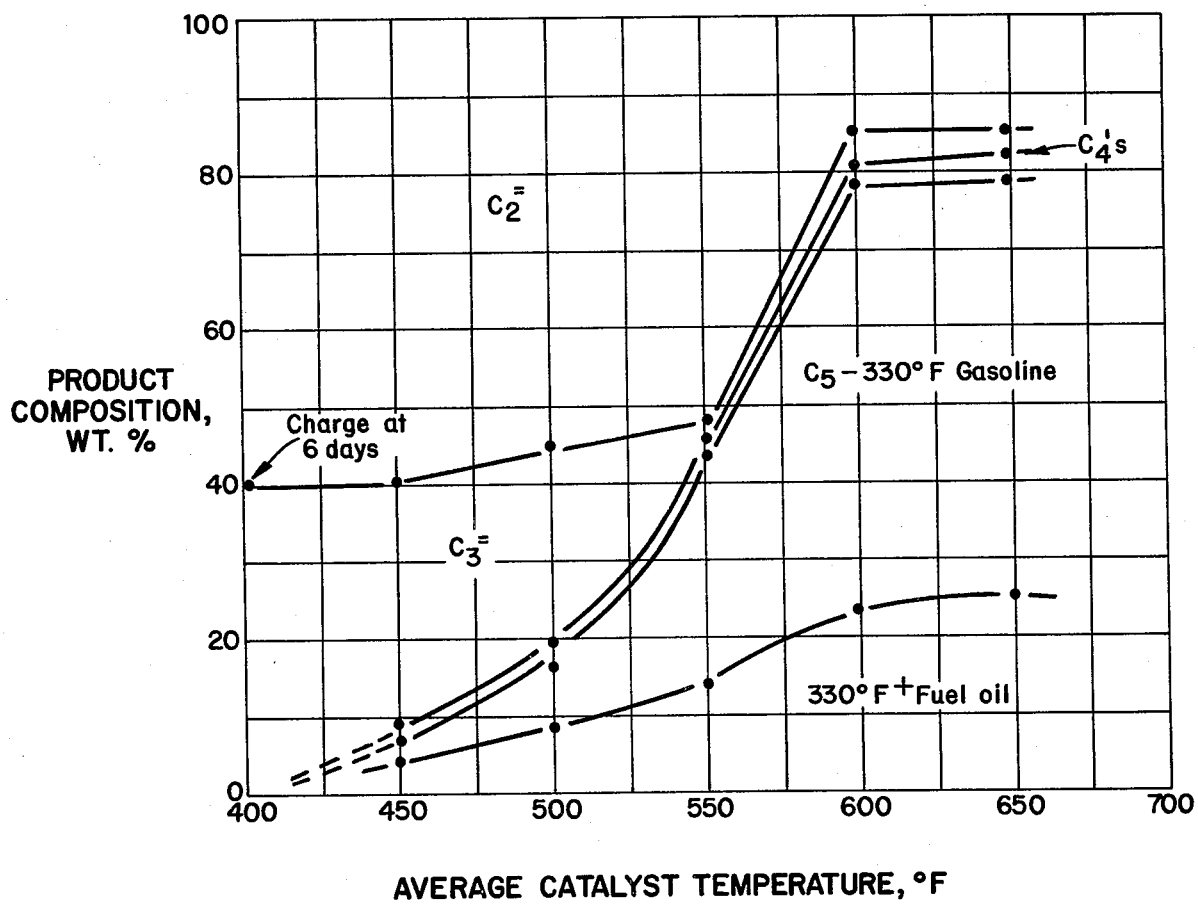
FIG. 2 represents a plot of product composition resulting from the conversion of FIG. 1.

The above table dramatically illustrates the novel process of this invention. In this connection, FIG. 1 represents a plot of the data obtained and FIG. 2 represents a plot of the product composition.

As can be seen, ethylene conversion was less than 10% at 450-550° F., whereas propylene rose from about 20% at 450° F. (Example 19) to greater than 90% at 550° F. (Example 21).

Thus, Example 21 demonstrates the severity needed to accomplish substantial conversion of propylene, i.e. greater than 80% while converting no more than 20 weight percent of ethylene.

Note that Examples 19, 20, 22 and 23 did not accomplish the selective conversion of $C_3$ and higher olefins in admixture of the same with ethylene. With regard to Example 23, the reaction conditions employed were outside the broad critical ranges previously set forth. It is noted, however, that the conditions of Examples 19, 20 and 22 fall within the broad ranges of temperature, pressure and space velocity previously set forth. This illustrates the difficulty in expressing the operable boundaries of this invention by simply reciting temperature, pressure and space velocity. As has been previously stated, it is necessary to use those temperatures, pressures and space velocities which will result in the substantial conversion, i.e greater than 80% and even more desirably, greater than 90% of $C_3$ and higher olefins to the substantial exclusion of the conversion of ethylene, i.e. less than 20%, and more preferably, less than 10%. Thus, for example, if one were to operate at the temperature and pressure specified in Example 19, one would have to decrease the weight hourly space velocity with regard to the propylene in order to obtain the severity of Example 21 so as to obtain the desired conversion of propylene. Again, by way of illustration, if one were to operate at the temperature and space velocity of Example 20, one would have to operate at a pressure higher than 400 psig in order to obtain the desired conversion.

What is claimed is:

1. In the process of contacting mixtures of $C_2$-$C_5$ olefins with an acidic crystalline aluminosilicate zeolite having a pore diameter greater than about 5 Angstroms, a silica-to-alumina ratio of at least 12, and a constraint index within the range of 1-12 at elevated temperatures, the improvement which comprises (a) carrying out said contact at a temperature of from about 300°-600° F., a pressure of from about 100-1,000 psig and at a space velocity with regard to $C_3$ and higher olefins ranging from about 0.1 to 10 WHSV; (b) said temperature, space velocity and pressure being chosen so as to convert at least 80% of the $C_3$ and higher olefins and no more than about 20 weight percent of said ethylene; (c) obtaining a product comprising both fuel oil and gasoline; and (d) recovering ethylene by flashing it off the higher boiling product.

2. The process of claim 1 wherein at least 90 weight percent of the $C_3$ and higher olefins are converted.

3. The process of claim 1 wherein no more than about 10 weight percent ethylene is converted.

4. The process of claim 1 wherein ethylene comprises at least 10 weight percent of the olefin mixture.

5. The process of claim 4 wherein the olefins are substantially a mixture of ethylene and propylene.

6. The process of claim 4 wherein a ZSM-5 type zeolite is used.

7. The process of claim 6 wherein the zeolite is ZSM-5.

8. The process of claim 6 wherein the zeolite is ZSM-11.

* * * * *